US011202645B2

(12) United States Patent
Stevens et al.

(10) Patent No.: US 11,202,645 B2
(45) Date of Patent: Dec. 21, 2021

(54) INTEGRATED CUTTING GUIDE WITH CARDIOPROTECTIVE BUTTERFLY FOR REPEAT STERNOTOMY AND FOR CAST CUTTING

(71) Applicant: Drexel University, Philadelphia, PA (US)

(72) Inventors: Randy Stevens, Merion Station, PA (US); Achintya Moulick, Philadelphia, PA (US); Vicki Mahan, North Wales, PA (US); Amy Throckmorton, Cherry Hill, NJ (US)

(73) Assignee: Drexel University, Philadelphia, PA (US)

( * ) Notice: Subject to any disclaimer, the term of this patent is extended or adjusted under 35 U.S.C. 154(b) by 453 days.

(21) Appl. No.: 16/031,307

(22) Filed: Jul. 10, 2018

(65) Prior Publication Data

US 2019/0008533 A1    Jan. 10, 2019

Related U.S. Application Data

(60) Provisional application No. 62/530,309, filed on Jul. 10, 2017, provisional application No. 62/577,569, filed on Oct. 26, 2017.

(51) Int. Cl.
*A61B 17/15* (2006.01)
*A61B 17/17* (2006.01)
(Continued)

(52) U.S. Cl.
CPC .......... *A61B 17/1789* (2016.11); *A61B 17/15* (2013.01); *A61B 17/823* (2013.01); *A61B 17/144* (2016.11); *A61B 2017/081* (2013.01)

(58) Field of Classification Search
CPC .......... A61B 2090/08021; A61B 90/04; A61B 17/823; A61B 17/15; A61B 17/1789;
(Continued)

(56) References Cited

U.S. PATENT DOCUMENTS

| 453,239 | A | * | 6/1891 | Hanchett | ................. | A61F 15/02 |
| | | | | | | 602/9 |
| 817,946 | A | * | 4/1906 | Williams | ................ | A61F 15/02 |
| | | | | | | 602/9 |

(Continued)

OTHER PUBLICATIONS

Prior Art Sternum saws. Undated. 1 page.
(Continued)

*Primary Examiner* — David W Bates
(74) *Attorney, Agent, or Firm* — Joseph E. Maenner; Maenner & Associates, LLC

(57) ABSTRACT

A cardioprotective patch with an integrated cutting guide includes a membrane having a top edge, a bottom edge distal from the top edge, a right side edge connecting the top edge and the bottom edge; and a left side edge, distal from the right side edge and connecting the top edge and the bottom edge. A fold extends parallel to the top edge about half way between the top edge and the bottom edge. The crease is slit from the right side edge, forming a right slit. An elongate frame is fixedly connected to the membrane. The frame includes a tubular member and a plurality of arms extending outwardly from the tubular member and connected to the membrane.

14 Claims, 10 Drawing Sheets

(51) Int. Cl.
*A61B 17/82* (2006.01)
*A61B 17/08* (2006.01)
*A61B 17/14* (2006.01)

(58) Field of Classification Search
CPC ............. A61B 17/1691; A61B 17/8076; A61F 2/2481; A61F 15/02
See application file for complete search history.

(56) References Cited

U.S. PATENT DOCUMENTS

| | | | | |
|---|---|---|---|---|
| 1,967,888 | A * | 7/1934 | Kearsley | A61F 15/02 30/1 |
| 2,187,175 | A * | 1/1940 | Prosperi | A61F 15/02 602/9 |
| 2,206,339 | A * | 7/1940 | Ulman, Jr. | A61F 15/02 602/9 |
| 2,523,837 | A * | 9/1950 | Luger | A61F 15/02 602/9 |
| 2,878,806 | A * | 3/1959 | French | A61F 15/02 602/9 |
| 3,643,657 | A * | 2/1972 | Whyte | A61F 15/02 602/9 |
| 3,867,931 | A * | 2/1975 | Babka | A61F 15/02 602/9 |
| 3,985,129 | A * | 10/1976 | Huene | A61F 15/02 602/9 |
| 4,041,941 | A * | 8/1977 | Driver | A61F 15/02 602/9 |
| 4,290,424 | A * | 9/1981 | Wahl | A61F 15/02 602/9 |
| 4,829,993 | A * | 5/1989 | Silvey | A61F 13/041 602/9 |
| 8,539,866 | B2 * | 9/2013 | Nayak | B23D 47/02 83/13 |
| 9,095,469 | B2 * | 8/2015 | Nayak | B23D 51/025 |
| 2002/0038124 | A1 * | 3/2002 | Lee | A61F 15/02 606/105.5 |
| 2009/0048480 | A1 * | 2/2009 | Klenk | A61B 17/00234 600/37 |
| 2011/0082459 | A1 * | 4/2011 | Aravot | A61B 17/1789 606/79 |
| 2011/0082498 | A1 * | 4/2011 | Deslauriers | A61B 17/00491 606/214 |
| 2011/0230810 | A1 * | 9/2011 | Raman | A61F 2/0063 602/44 |
| 2012/0226320 | A1 * | 9/2012 | Kang | A61B 17/8085 606/283 |
| 2013/0296753 | A1 * | 11/2013 | Perrier | A61F 15/02 602/9 |
| 2015/0045906 | A1 * | 2/2015 | Schumacher | A61B 17/68 623/23.61 |
| 2016/0331388 | A1 * | 11/2016 | Garfein | A61B 17/8869 |
| 2018/0177642 | A1 * | 6/2018 | Anderson | A61F 13/04 |
| 2019/0069938 | A1 * | 3/2019 | Martinez-Ferro | A61B 17/8076 |

OTHER PUBLICATIONS

Ran, Lydia, et al., "Innominate Artery Cannulation Access in Pediatric Patients Undergoing Redo Sternotomy", World Journal of Cardiovascular Surgery, 2016, 6, 112-116.

* cited by examiner

INTEGRATED CUTTING GUIDE WITH CARDIOPROTECTIVE BUTTERFLY FOR REPEAT STERNOTOMY AND FOR CAST CUTTING

CROSS-REFERENCE TO RELATED APPLICATION

The present application claims the benefit of U.S. Provisional Patent Application Ser. No. 62/530,309, filed on Jul. 10, 2017 and U.S. Provisional Patent Application Ser. No. 62/577,569, filed on Oct. 26, 2017, both of which are incorporated herein by reference in their entireties.

BACKGROUND OF THE INVENTION

Pericardial patches are used prior to closing up a patient's sternum after a sternotomy. A sternotomy can be performed to access internal organs (heart, lungs, etc.) for surgery or other procedure. The pericardial patch is placed between the organs and the sternum to prevent scar tissue from the organs from adhering to the sternum, which can cause a dangerous condition for the patient if a repeat sternotomy must be performed. A known pericardial patch is manufactured by W. L. Gore and Associates. Additionally, it can sometimes be necessary to perform a repeat sternotomy.

It would be beneficial to provide a pericardial patch that can reduce complications associated with a repeat sternotomy, as well as to provide a mechanism integrated into the patch to assist in performing the repeat sternotomy. As an added benefit, it would be beneficial to apply the mechanism to cutting a cast, such as to remove a cast after the healing of a broken limb.

BRIEF SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a cardioprotective patch with an integrated cutting guide that includes a membrane having a top edge, a bottom edge distal from the top edge, a right side edge connecting the top edge and the bottom edge; and a left side edge, distal from the right side edge and connecting the top edge and the bottom edge. A fold extends parallel to the top edge about half way between the top edge and the bottom edge. The crease is slit from the right side edge, forming a right slit. An elongate frame is fixedly connected to the membrane. The frame includes a tubular member and a plurality of arms extending outwardly from the tubular member and connected to the membrane.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
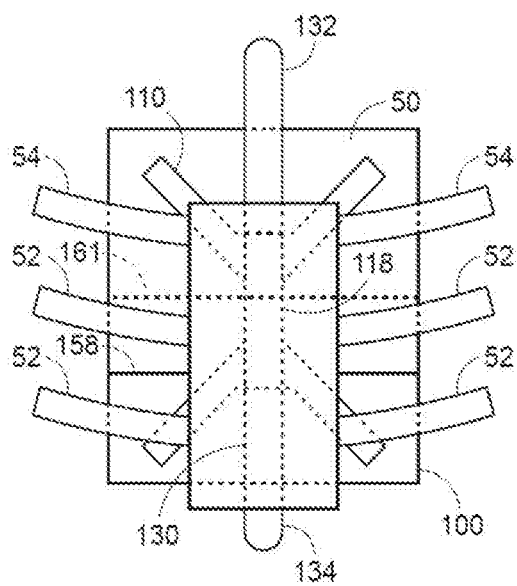
FIG. 1 is a top plan view of a cardioprotective butterfly according to an exemplary embodiment of the present invention implanted below a patient's sternum.

In the drawings, like numerals indicate like elements throughout. Certain terminology is used herein for convenience only and is not to be taken as a limitation on the present invention. The terminology includes the words specifically mentioned, derivatives thereof and words of similar import. As used herein the terms "top" and "upward" are defined as directions closer to a patient's head and the terms "bottom" and "downward" are defined as directions closer to the patient's feet.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

As shown in the Figures, a cardioprotective butterfly 100 ("butterfly 100") for repeat sternotomies is provided. Those skilled in the art, however, will recognize that butterfly 100 can be used for an initial sternotomy. Butterfly 100 is particularly applicable for use with neonatal and pediatric patients who experience rapid growth over relatively short periods of time, requiring a device that can "grow" with the patient. While butterfly 100 can be used for neonatal and pediatric patients, this does not exclude the use of butterfly 100 for adult patients as well.

Figure 2:
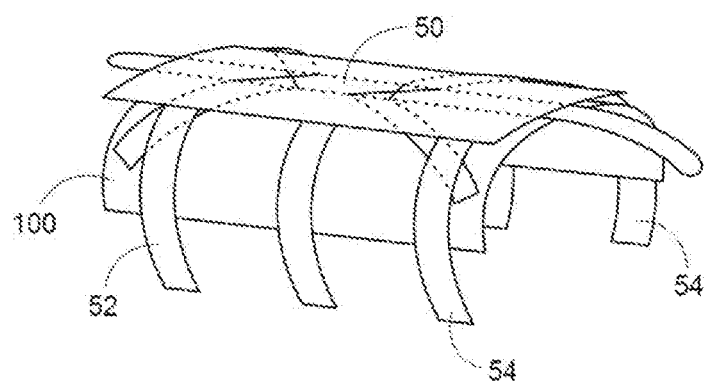
FIG. 2 is a side perspective view of the cardioprotective butterfly shown in FIG. 1 implanted below the patient's sternum.

As shown in FIGS. 1 and 2, butterfly 100 is implanted into a patient below a sternum 50, ribs 52, and clavicle 54 while closing up a sternotomy to facilitate cardiac access in the event that a repeat sternotomy is required. Butterfly is implanted between the patient's organs and chest wall to allow safer reentry into the patient's chest cavity during the repeat sternotomy.

Figure 3:
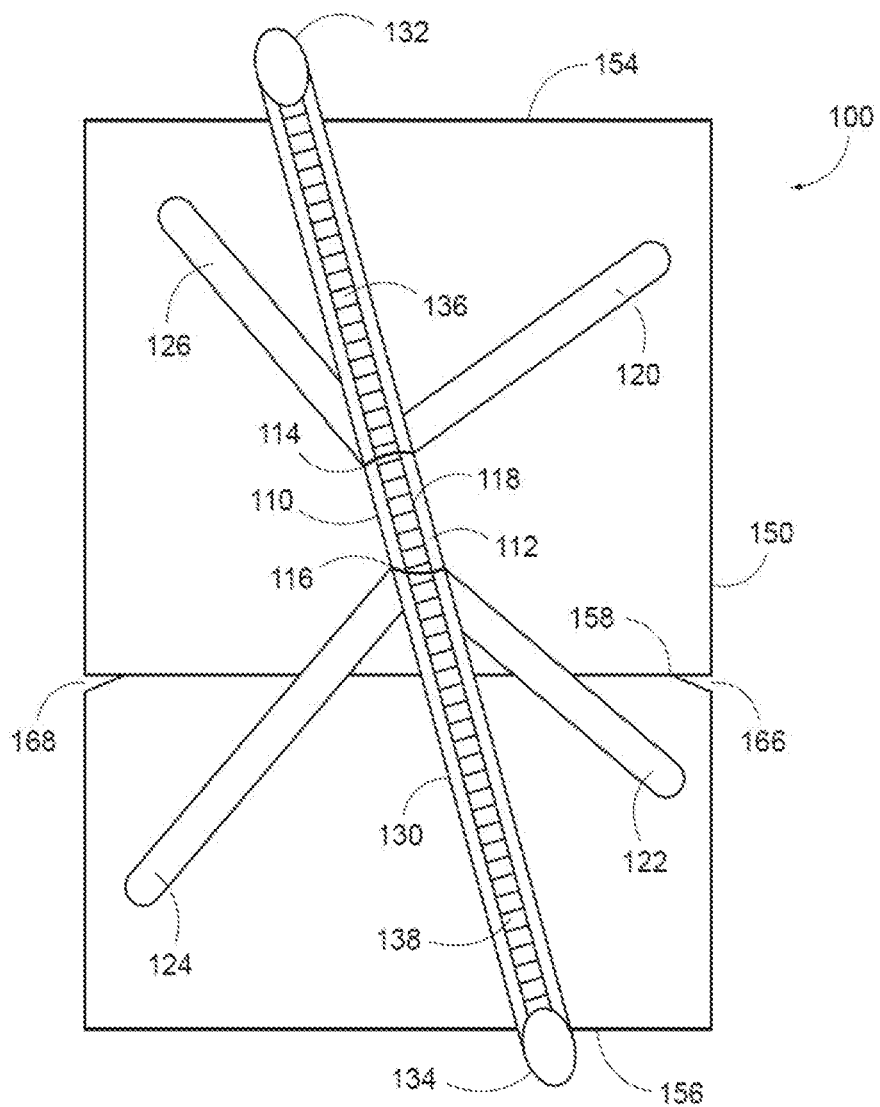
FIG. 3 is a top plan view of the cardioprotective butterfly shown in FIG. 1.

Referring to FIG. 3, butterfly 100 includes a frame 110 and a flexible material such as a membrane 150. Frame 110 includes an elongate tubular member 112 having an open top end 114, an open bottom end 116, and a through passage 118 extending between top end 114 and bottom end 116. In an exemplary embodiment, through passage 118 has a diameter of about 3.5 mm.

Four "arms" 120, 122, 124, 126 extend outwardly from tubular member 112. In an exemplary embodiment, arms 120-126 can be generally flat and can be formed from tubular member 112 by splitting tubular member 112 lengthwise at top end 114 to form arms 120, 126 and from bottom end 116 to form arms 122, 124. Arms 120-126 are fixedly connected to membrane 150, such as by adhesive, suture, or other securing device.

Arm 120 extends from top end 114 at an oblique angle upward and to the right of tubular member 112, arm 122 extends from bottom end 116 at an oblique angle downward and to the right of tubular member 112, arm 124 extends from bottom end 116 at an oblique angle downward and to the left of tubular member 112, and arm 126 extends from top end 114 at an oblique angle upward and to the left of tubular member 112. If frame 110 is placed on an analog clock with top end 114 at 12:00 and bottom end 116 at 6:00, then arm 120 is at about 1:30, arm 122 is at about 4:30, arm 124 is at about 7:30 and arm 126 is at about 10:30.

A securing member 130 is slidably inserted into through passage 118. Securing member 130 has a top end 132, a bottom end 134, and a body 136 extending between top end 132 and bottom end 134. Body 136 can be accordion-shaped such that body 136 can self-expand as sternum 50 grows. Securing member 130 can be hollow, with a through passage 138 extending between top end 132 and bottom end 134. To accommodate the accordion-shape aspect of body 136, securing member 130 can be a hollow tube.

In an exemplary embodiment, securing member 130 is sufficiently longer than tubular member 112 so that top end 132 extends outwardly from top end 114 and that bottom end 134 extends outwardly of bottom end 116. When butterfly 100 is implanted underneath sternum 50, top end 132 extends above sternum 50 and bottom end 134 extends below sternum 50. Top end 132 can be folded over sternum 50 such that top end 132 is pointing downward and bottom end 134 can be folded over sternum 50 such that bottom end 134 is pointing upward. Each of top end 132 and bottom end 134 can be secured to sternum 50, such as by staples, sutures, or other securing mechanism.

Frame 110 and securing member 130 can each be constructed from a flexible medical grade material, such as, for example nylon, PTFE (TEFLON®), and polyurethane composite, such as, for example GORETEX®, although those skilled in the art will recognize that other medical grade materials can be used.

Figure 4:
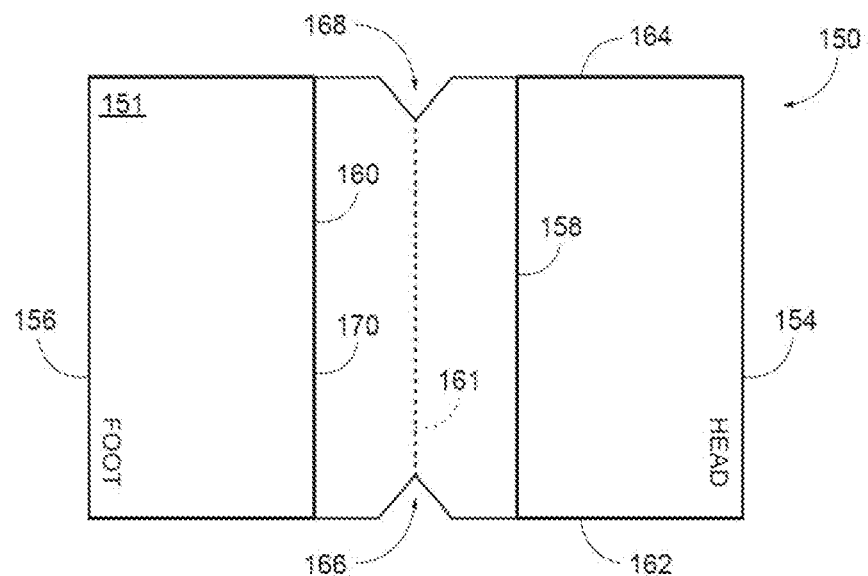
FIG. 4 is a top plan view of the membrane used with the cardioprotective butterfly shown in FIG. 3.

Referring to FIG. 4, membrane 150 is a single, generally rectangular sheet of material having an upper surface 151, a smooth lower surface 152, and a thickness between upper surface 151 and lower surface of about 0.6 mm. Lower surface 152 is in contact with the patient's heart (not shown) after butterfly 100 is implanted. In an exemplary embodiment, lower surface 152 is constructed from a nylon, PTFE, and GORETEX®. Optionally, lower surface 152 can also be coated with an anticoagulant, such as heparin, to inhibit cell attachment to lower surface 152. Further, it is desired that no obstructions, such as sutures, are present on lower surface 152 that might enhance or encourage cell adhesion thereto.

Figure 5:
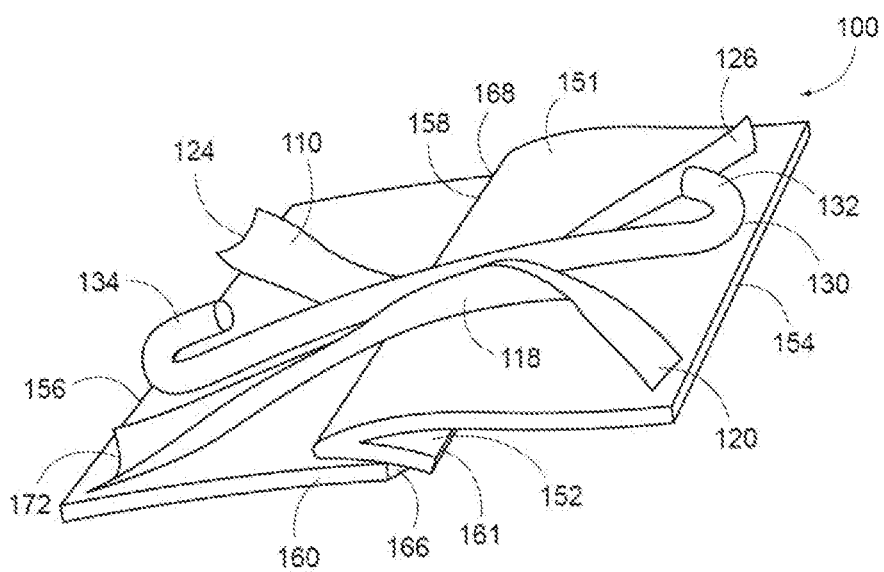
FIG. 5 is a side perspective view of the cardioprotective butterfly shown in FIG. 3, showing a slit for a chest tube and/or other inserted devices.

Membrane 150 is generally rectangular in shape and includes a top edge 154, a bottom edge 156, and a crease 158. Crease 158 extends parallel to top edge 154 and bottom edge 156, and extends about ⅓ the distance from top edge 154 toward bottom edge 156. As shown in FIG. 5, crease 158 is folded over top surface 151 to a fold line 160 that is about ⅓ the distance from bottom edge 156 toward top edge 154, shown in FIG. 5, forming a fold 161 about half way between top edge 154 and bottom edge 156.

Membrane 150 also includes a right side edge 162 and an opposing left side edge 164. Right side edge 162 and left side edge 164 each extends between top edge 154 and bottom edge 156. Fold 161 is slit from right side edge 162, forming a slit 166. Similarly, fold 161 is slit from left side edge 164, forming a slit 168. A central portion 170 of fold 161 between slits 166, 168 maintains membrane 150 as a single piece.

When membrane 150 is folded along fold 161 and crease 158 such that crease 158 is in contact with fold line 160, slits 166, 168 provide a passage between upper surface 151 and lower surface 152 to allow for the insertion of chest tubes 60, pacing wires, or other devices through either slit 166, 168 to facilitate the drainage of thoracic content. Fold 161 allows membrane 150 to extend between top edge 154 and bottom edge 156 to accommodate growth of the patient while butterfly 100 is implanted in the patient.

To ensure correct implantation orientation of butterfly 100, it may be desired to print indicia on upper surface 151 near top edge 154 that indicates the top of membrane 150. For example, the word "TOP" or "HEAD" in one or more languages, or a representation of a head can be printed on near top edge 154. Similarly, it may be desired to print indicia on upper surface 151 near bottom edge 156 that indicates the bottom of membrane 150. For example, the word "BOTTOM" or "FOOT" in one or more languages, or a representation of a foot can be printed on near bottom edge 156. See FIG. 4 for exemplary indicia. It is important to ensure correct implantation orientation so that chest tubes 60 can be properly inserted from fold line 160, through slits 166, 168, and into the patient. If membrane 150 is too large, membrane 150 can be cut prior to implantation in the chest cavity.

In an exemplary embodiment, frame 110 is connected to membrane 150 with sutures that extend around frame 110 and are tied to membrane 150 proximate to crease 158 such that, when membrane 150 is folded along crease 158, the sutures extend between crease 158 and fold 161 when membrane 150 is folded as shown in FIG. 5, so that no sutures are exposed to the chest cavity. Additionally, arms 122, 124 are attached to membrane 150 proximate to bottom edge 156. While sutures are an exemplary connecting device, those skilled in the art will recognize that other connection means, such as clips, or by fusing frame 110 to membrane 150 (via heat, chemical or other means), can be used.

Figure 6:
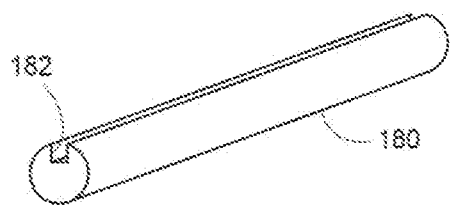
FIG. 6 is a perspective view of an exemplary saw guide used with the cardioprotective butterfly shown in FIG. 3.
Figure 7:
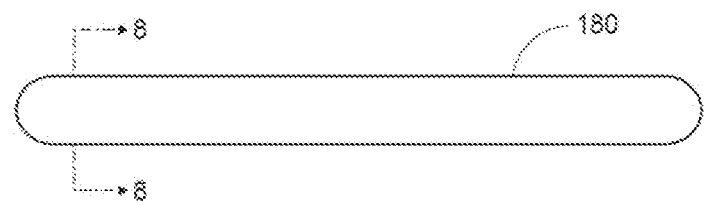
FIG. 7 is a side elevational view of the saw guide shown in FIG. 6.
Figure 8:
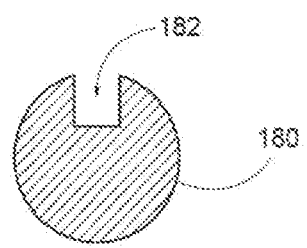
FIG. 8 is a front elevational view of the saw guide shown in FIG. 6.

Referring to FIGS. 6-8, a saw guide 180 is also provided to assist in re-cutting sternum 50 in the event of a repeat sternotomy. Saw guide 180 is a cylindrical insert that is insertable into through passages 118, 138, and is longer than sternum 50 such that saw guide 180 extends both above the top of sternum 50 and below the bottom of sternum 50 when saw guide 180 is inserted into through passages 118, 138. Optionally, one end of saw guide 180 can be tapered to facilitate insertion of saw guide 180 into through passages 118, 138. Saw guide 180 can be constructed from a relatively pliable material, such as rubber or a soft plastic, and has a smaller diameter than the diameter of through passages 118, 138. In an exemplary embodiment, saw guide 180 has a diameter of about 3 mm. Saw guide 180 is used to guide a saw blade assembly 190 when cutting sternum 50 during a repeat sternotomy.

Figure 9:
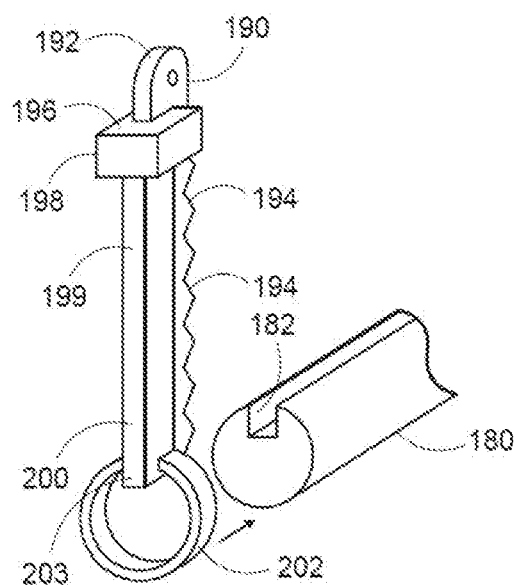
FIG. 9 is a perspective view of an exemplary saw blade assembly and saw guide for use with the saw guide shown in FIG. 6.
Figure 10:
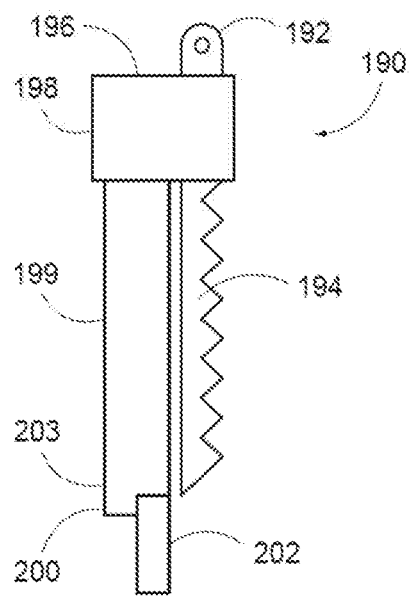
FIG. 10 is a side elevational view of the saw blade assembly shown in FIG. 9.

As shown in FIG. 8, saw guide 180 has a generally cylindrical cross section and includes a saw channel 182 extending the length thereof. While an exemplary cross-section is cylindrical, those skilled in the art will recognize that the cross-section can be other shapes as well, such as an oval or rectangular geometry, which may provide better stability and ease of insertion of saw guide 180 into through passages 118, 138. Saw channel 182 extends about ⅓ into saw guide 180 and has a width greater than the width of saw blade assembly 190, shown in FIGS. 9 and 10. Optionally, saw guide 180 can include a bottom handle (not shown) to allow a clamp (not shown) to grasp bottom handle while using saw blade assembly 190 with saw guide 180.

Saw blade assembly 190 can be used with a reciprocating or oscillatory saw handle (not shown). Saw blade assembly 190 includes a reciprocating blade 192 having teeth 194 that extend axially along blade 192. Teeth 194 have a width less than the width of saw channel 182 to enable distal teeth 194 on blade 192 to fit into saw channel 182.

A proximal end 196 of saw blade assembly 190 includes a shank 198 that extends into and is secured by the saw. A distal end 200 of fixed shaft 199 includes a loop 202 having an opening 204 formed therein. Loop 202 extends in a plane perpendicular to the direction of teeth 194 extending from blade 192. Additionally, the diameter of saw guide 180 is sufficiently smaller than the inner diameter of tubular member 112 such that loop 202 can fit between saw guide 180 and tubular member 112 so that loop 202 can readily advance along saw guide 180 during the cutting procedure.

Loop 202 has an inner perimeter that is shaped to match the cross-sectional shape of saw guide 180, with at least a slight clearance between the inner perimeter of loop 202 and saw guide 180 to allow loop 202 to readily slide along saw guide 180. Additionally, the inner diameter of tube 210 is sufficiently larger than the outer diameter/perimeter of loop 202 so that tube 210 does not impede the advancement of the saw blade assembly 190 during cutting of tube 210. Optionally, the side of loop 202 facing in the direction of saw blade teeth 194 can have a conical/tapered shape to facilitate the advancement of saw blade assembly 190 into tube 210 during cutting.

Distal end 200 of shaft 199 also includes a tang 203 that extends into loop 202. Tang 203 is sized to fit into saw channel 182 such that saw channel 182 guides saw blade assembly 190 along the length of saw guide 180. Tang 203 prevents saw blade assembly 190 from rotating with respect to saw guide 180 as saw blade assembly 190 is advanced along saw guide 180. In operation, as blade 192 reciprocates in an up and down direction, shaft 199 with loop 202 remains stationary.

To implant butterfly 100 after a sternotomy, butterfly is inserted into the patient's chest cavity between the two halves of a longitudinally sliced sternum 50 such that top edge 154 is located toward the patient's head, bottom edge 156 is located toward the patient's feet, and lower surface 152 is located toward the patient's heart. Securing member 130 is extended such that top end 132 extends above sternum 50 and bottom end 134 extends below sternum 50.

Optionally, a stabilizing material (not shown) can be inserted into securing member 130. The stabilizing material can be a solid material or a liquid, such as saline, that prevents the compression of securing member 130 and tubular member 112 while butterfly 100 is in the patient.

After sternum 50 is reconnected, such as by surgical wire and/or staples (not shown), top end 132 is folded down and secured to sternum 50. Similarly, bottom end 134 is fold up and secured to sternum 50. As the patient grows, body 136 can expand to accommodate the lengthening of sternum 50 without securing member 130 being torn from sternum 50.

Figure 11:
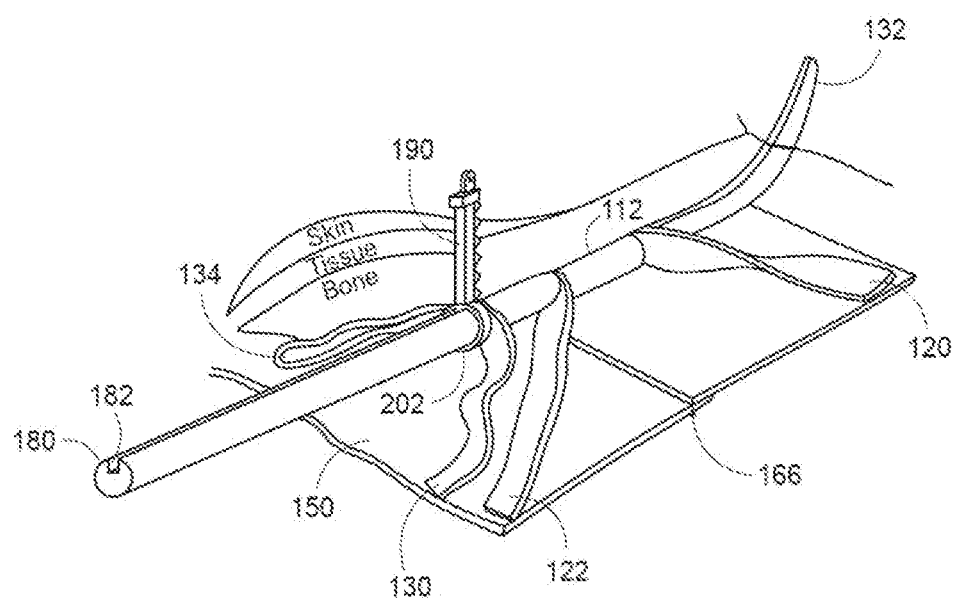
FIG. 11 is a perspective view showing the cardioprotective butterfly shown in FIG. 3 being cut away using the saw guide shown in FIGS. 6-8 and the saw blade shown in FIGS. 9 and 10.
Figure 12:
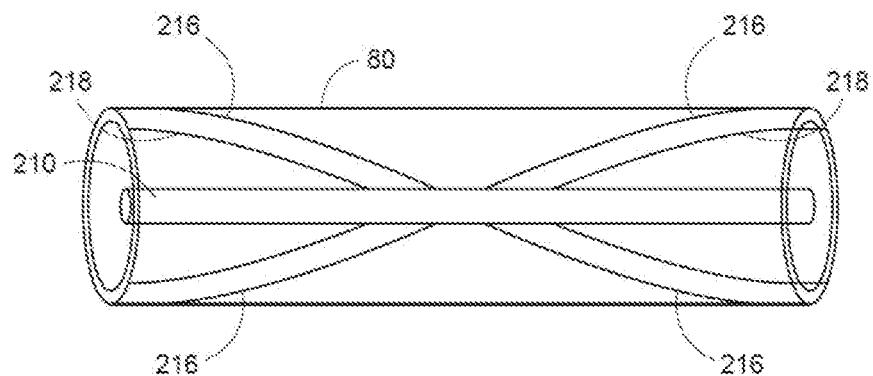
FIG. 12 is a side elevational view of a guide according to an exemplary embodiment of the present invention used with a cast.

In the event of a repeat sternotomy, after accessing sternum 50, securing member 130 is disconnected from sternum 50 by removing staples or sutures that secure top end 132 and bottom end 134 of securing member 130 to sternum 50. If any stabilizing material has been inserted into securing member 130, the stabilizing material is then removed. Securing member 130 can then be slid out of through passage 118 and discarded. Alternatively, securing member 130 can remain inside tubular member 112 and cut, as shown in FIG. 11.

Saw guide 180 is inserted into through securing member 130 and passage 118 in tubular member 112, with saw channel 182 facing up toward sternum 50. Distal end 200 of shaft 199 is inserted into saw channel 182 and loop 202 is looped around saw guide 180 so that saw guide 180 extends through opening 204 in loop 202.

The saw is operated such that teeth 194 of saw blade 192 reciprocate to cut through sternum 50, while shaft 199 and loop 202 do not reciprocate, as saw blade assembly 190 is advanced from the bottom of sternum 50 upward. Loop 202 slides along saw guide 180 until loop 202 engages bottom end 116 of tubular member 112, at which time loop 202 is advanced between saw guide 180 and tubular member 112, where saw blade assembly 190 slices tubular member 112 as saw blade assembly 190 is advanced. While a "bottom-up" procedure is described, those skilled in the art will recognize that a "top-down" procedure can be performed within the scope of this disclosure.

After sternum 50 is fully cut, saw guide 180 can be slid from tubular member 112 and saw blade assembly 190 can be pulled out of the patient, allowing butterfly 100 to be removed from the patient.

Saw guide 180 and saw blade assembly 190 can be used not only for a repeat sternotomy, as discussed above but, referring to FIGS. 12-18, saw guide 180 can also be incorporated into a cast 80 as an integrated cast cutting guide in order to reduce the likelihood or even eliminate the chance of inadvertently cutting the patient's skin when removing cast 80.

Figure 13:
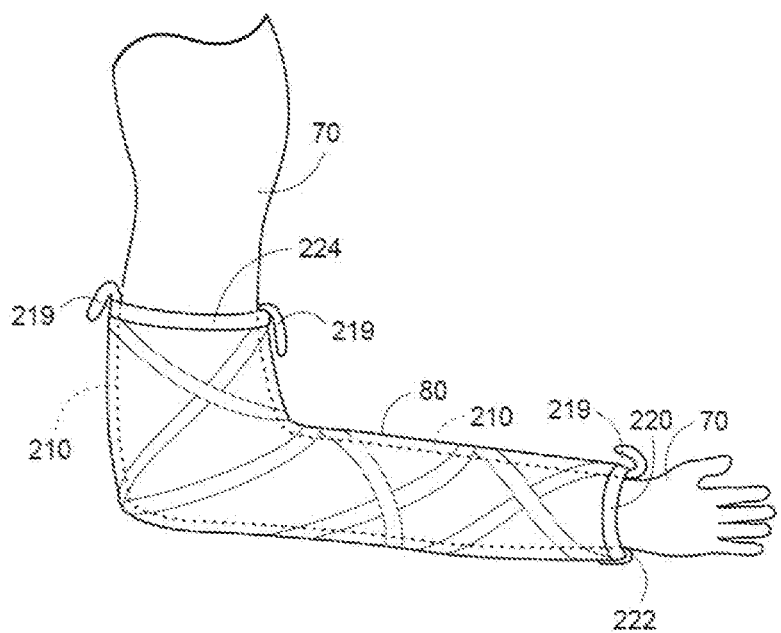
FIG. 13 is a side elevational view of the guide and cast shown in FIG. 12 around a patient's arm.
Figure 14:
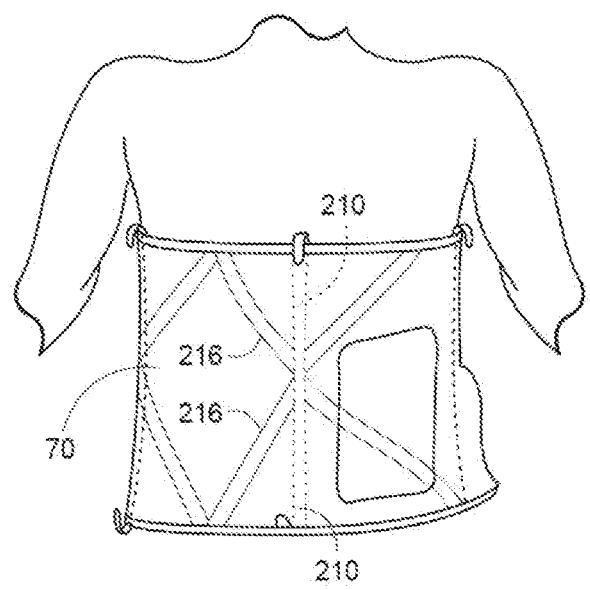
FIG. 14 is a side elevational view of view of the guide and cast shown in FIG. 12 around a patient's waist.

Referring to FIGS. 13 and 14, a hollow tube 210 can be applied to cast 80 when cast 80 is being applied to set a broken bone such as, for example, a radius of an arm 80. In another exemplary application, tube 210 can be applied to cast 80 that is placed around a patient's waist, such as after abdominal surgery.

Figure 15:
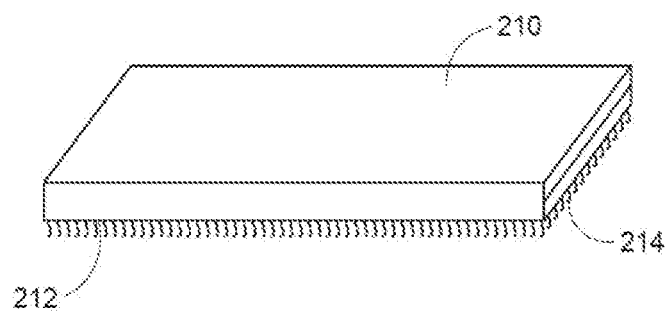
FIG. 15 is a perspective view of the tube shown in FIG. 12 in a compressed condition.

Tube 210 can be constructed from an impermeable, yet pliable material, such as a polymer, to allow tube 210 to compress as shown in FIG. 15, and not allow moisture, such as water or other casting liquid from cast 80 while cast is still wet and being applied to a patient or sweat from the patient to permeate tube 210.

Figure 16:
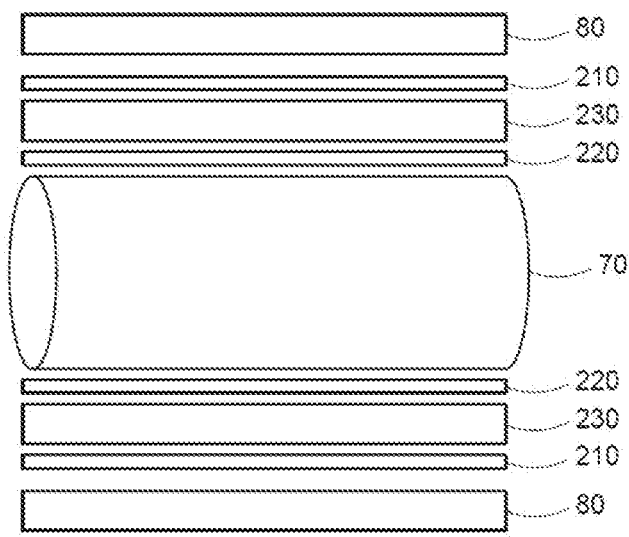
FIG. 16 is an exploded view of the guide and cast shown in FIG. 12; d

Referring to FIG. 16, an exemplary schematic showing where tube 210 is located within cast 80 is shown. Arm 70 (or other body part) is centrally located, with a stockinette 220 stretched over the patient's skin. Stockinette 220 can be a soft woven fabric material, such as a single layer of gauze, or other suitable material to provide a barrier to the patient's skin. Stockinette 220 is sufficiently long so that each end 222, 224 of stockinette 220 can be turned and folded over cast 80, as shown in FIG. 13.

A next layer can be a flexible material, such as a "fluff" layer 230 that can include gauze, cotton based material, or any other soft compressible material. Tube 210 is then applied over layer 230. Tube 210 in it compressed condition, as shown in FIG. 15, includes a bottom surface 212 having a plurality of small hooks 214, similar to the hooks of a hook and loop fastener, commonly known as Velcro®. Layer 230, therefore, has a plurality of loops formed on the outer surface thereof, such that tube 210 releasably adheres to fluff layer 230 to prevent tube 210 from inadvertently slipping during or after application of tube to fluff layer 230.

Tube 210 also includes a plurality of support arms 216 that extend at oblique angles therefrom. Similar to bottom surface 212 of tube 210, a bottom surface 218 of support arms 216 includes a plurality of hooks 214 to engage fluff layer 230. Support arms 216 are sufficiently long to wrap at least 180 degrees around arm 70 and can be cut to length if desired or required. Arms 216 also allow for lifting and stabilizing tube 210 during the sawing/removal process.

Additionally, tube 210 is provided longer than required for the length of cast 80 to be applied so that each end 219 of tube 210 can be folded over after cast 80 is applied to prevent debris from entering tube 210 and to provide an easy access to tube 210 when the time comes to remove cast 80. After tube 210 is placed, cast 80 is applied over tube 210 and fluff layer 230. Ends 222, 224 of stockinette 220 can then be folded over cast 80, as shown in FIG. 13.

Figure 17:
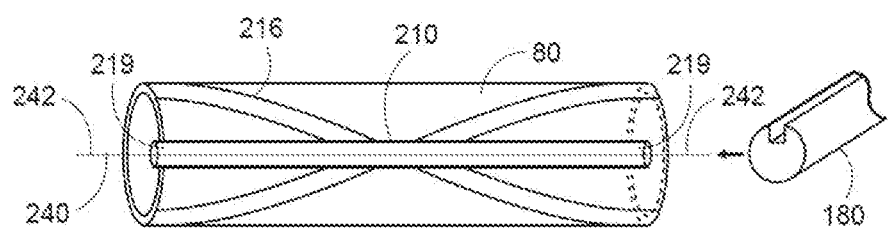
FIG. 17 is a perspective view of a guide wire inserted through the tube of FIG. 12 during the cast cutting process.

To cut cast 80 away from arm 80 (or whatever body part has been casted), a clinician unfolds ends 219 of tube 210 and, as shown in FIG. 17, inserts a guide member 240 into one of ends 219 and pushes guide member 240 through tube 210 until guide member 240 exits from the other end 219 of tube 210. The clinician then attaches saw guide 180 to an end 242 of guide member 240 and pulls the other end 244 of guide member 240 outwardly from tube 210, which draws saw guide 180 into tube 180, expanding tube 210 so that saw guide 180 can traverse the length of tube 210. Guide member 240 can be a guide wire, as shown in FIG. 17. Alternatively, guide member 240 can be a flat plate already inserted into tube 210 prior to the casting process.

After saw guide 180 is fully inserted into tube 210, saw blade assembly 190 is slid over saw guide 180 as described above and shown in FIGS. 9 and 11. Saw blade assembly 190 is attached to a reciprocating saw (not shown) and advanced along saw guide 180 such that saw blade assembly 190 cuts through cast 80. As blade 192 reciprocates up and down, teeth 194 cut through cast 80. Shank 199 and loop 202 remain stationary and only advance through cast 80 as the saw is advanced through cast 80.

If cast 80 bends at a body joint, such as an elbow, as shown in FIG. 13, saw blade assembly 190 can be advanced to a point near the joint and stopped. Saw blade assembly 190 can be backed out of cast 80, inserted at the other end of saw guide 180, where the process is repeated until saw blade assembly 190 is again advanced to a point near the joint and stopped. Saw blade assembly 190 and saw guide 180 can be removed from tube 210 and any remaining portion of cast 80 near the joint that has not yet been cut can be easily snipped and removed.

Alternatively, although not shown, guide member 240 can be provided already inside tube 210 and tube 210 with guide member 240 can be applied during the casting process. Then, when it is time to remove cast 80, saw guide is simply attached to guide member 240 as described above, and the remainder of the above-described cast removal process is performed.

Figure 18:
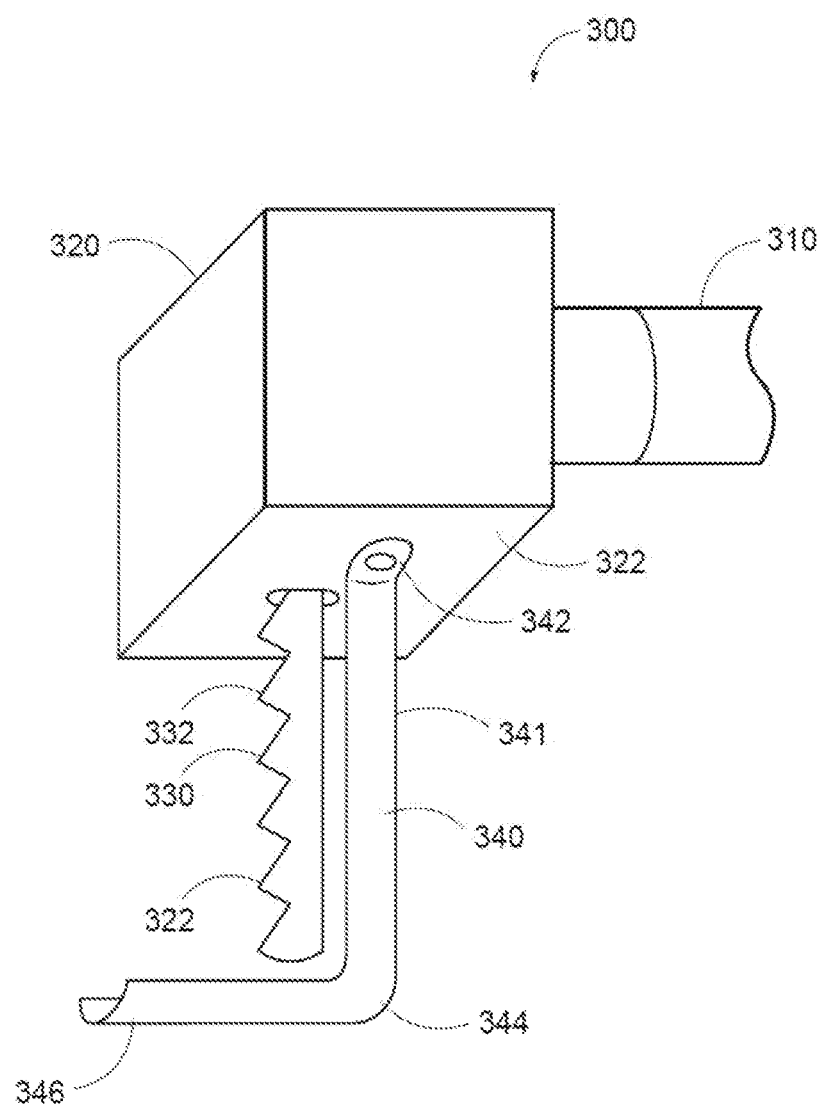
FIG. 18 is a perspective view of an exemplary saw blade assembly and saw guide for attachment to a drive according to an alternative exemplary embodiment of the present invention.

FIG. 18 shows an alternative embodiment of an exemplary saw blade assembly and saw guide 300 (assembly 300") according to an exemplary embodiment of the present invention. Assembly 300 can be used to cut either the tubular member 112 or tube 210 discussed above.

Assembly 300 can be driven by a driver 310 such as, for example, a direct coupling to the output of a drill, an indirect drive through a flexible drive extension, or other rotating device. The drill (not shown) can be AC or DC powered and the flexible drive extension (not shown) can be coupled to a high speed drill (not shown). The high speed drill can be located distal from assembly 300 and optionally located in a sound proof enclosure to eliminate sounds from the drill when the drill is in operation. Optionally, the drill can be operated by a foot pedal (not shown) to allow the operator to use both hands without having to concentrate on starting/stopping the drill with a hand.

A rotation-to-reciprocation adapter 320 converts the rotary output of the drill to a reciprocating motion. Such adapters 320 are well known in the art and can be purchase commercially. A saw blade 330 is fixed to adapter 320 such that operation of adapter 320 results in a reciprocating motion of saw blade 330.

A saw guide 340 includes a shank 341 that is fixed to the bottom 322 of adapter 320 at a proximal, or fixed, end 342 and extends downwardly and behind the saw blade 330 such that teeth 332 of saw blade 330 are in front of shank 341, past the length of travel of saw blade 330 to a distal, or free, end 344. A trough-shaped guide 346 extends generally orthogonally from saw guide 340 toward and past saw blade 330 such that an axis of reciprocation of the saw blade 330 extends through guide 346.

To use assembly 300, saw guide 180 can be omitted from butterfly 100 or cast 80 when cutting sternum 50 or cast 80 as described above. Instead, guide 346 is inserted into either through passages 118, 138 or tube 210 and drill is started, reciprocating saw blade 330. Assembly 300 is advanced through passages 118, 138 or tube 210 so that saw blade 330 can cut sternum 50 or cast 80 as described above.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A cardioprotective patch with an integrated cutting guide comprising:
   a membrane having:
      a top edge;
      a bottom edge distal from the top edge;
      a right side edge connecting the top edge and the bottom edge;
      a left side edge, distal from the right side edge and connecting the top edge and the bottom edge;
      a fold extending parallel to the top edge about half way between the top edge and the bottom edge, forming a crease, wherein the crease is slit from the right side edge, forming a right slit; and
   an elongate frame fixedly connected to the membrane, wherein the frame includes:
      a hollow tubular member forming the cutting guide;
      a plurality of arms extending outwardly from the tubular member and connected to the membrane.

2. The cardioprotective patch with integrated cutting guide according to claim 1, wherein the crease is slit from the left side edge, forming a left slit.

3. The cardioprotective patch with integrated cutting guide according to claim 2, wherein the fold further comprises a central portion between the right slit and the left slit.

4. The cardioprotective patch with integrated cutting guide according to claim 1, wherein the frame further comprises a securing member extending though the tubular member.

5. The cardioprotective patch with integrated cutting guide according to claim 4, wherein the securing member has a first tubular member end extending past the top edge of the membrane and a second tubular member end extending past the bottom edge of the membrane.

6. The cardioprotective patch with integrated cutting guide according to claim 4, further comprising a saw guide adapted to be inserted into the securing member.

7. The cardioprotective patch with integrated cutting guide according to claim 6, wherein the saw guide comprises an elongate member having a saw channel extending the length of the member.

8. The cardioprotective patch with integrated cutting guide according to claim 7, further comprising a saw blade assembly, the saw blade assembly comprising a shank and a loop extending from the shank, such that the loop is sized to slide over the elongate member.

9. The cardioprotective patch with integrated cutting guide according to claim 8, wherein the saw blade assembly further comprises a saw blade adapted to fit into the saw channel as the loop slides over the elongate member.

10. The cardioprotective patch with integrated cutting guide according to claim 6, wherein the saw guide comprises a trough shape.

11. The cardioprotective patch with integrated cutting guide according to claim 10, wherein the saw guide is attached to a rotation-to-reciprocation adapter, and wherein a saw blade is operatively connected to the rotation-to-reciprocation adapter.

12. A medical device comprising:
    a flexible material;
    a tubular member attached to the flexible material;
    a plurality of support members extending outwardly from the tubular member, wherein each of the support members is also attached to the flexible material;
    a securing member extending though the tubular member, the securing member comprising a hollow tube, wherein the securing member is configured to secure the flexible material to a portion of a patient; and
    a saw guide insertable into the securing member, wherein the saw guide has a generally cylindrical cross section and includes a saw channel extending the length thereof, the saw channel configured to receive a portion of a saw blade assembly therein, wherein the saw guide is adapted to guide a saw of the saw blade assembly along the length of the securing member.

13. The medical device according to claim 12, wherein the saw guide comprises an elongate rod.

14. The medical device according to claim 12, wherein the saw guide is attached to a saw blade.

* * * * *